US006693417B2

(12) United States Patent
Wilson

(10) Patent No.: US 6,693,417 B2
(45) Date of Patent: Feb. 17, 2004

(54) MICRO-ELECTRONIC BOND DEGRADATION SENSOR AND METHOD OF MANUFACTURE

(75) Inventor: Alan Wilson, Victoria (AU)

(73) Assignee: Commonwealth of Australia, Canberra (AU)

( * ) Notice: Subject to any disclaimer, the term of this patent is extended or adjusted under 35 U.S.C. 154(b) by 0 days.

(21) Appl. No.: 10/139,035

(22) Filed: May 3, 2002

(65) Prior Publication Data

US 2002/0190729 A1 Dec. 19, 2002

Related U.S. Application Data

(62) Division of application No. 09/501,798, filed on Feb. 8, 2000, now Pat. No. 6,384,610.
(60) Provisional application No. 60/119,166, filed on Feb. 8, 1999.

(51) Int. Cl.[7] .............................. G01R 1/00; C25D 5/00
(52) U.S. Cl. ...................... 324/158.1; 205/81; 205/123; 204/228.7; 204/229.8
(58) Field of Search .................. 204/229.8, 229.9, 204/230.8, 228.7; 205/96, 81, 123, 83; 438/155; 324/522, 713, 769, 663, 691, 158.1, 765, 766, 719

(56) References Cited

U.S. PATENT DOCUMENTS

| | | | |
|---|---|---|---|
| 4,423,371 A | 12/1983 | Senturia et al. | 324/61 |
| 4,906,346 A | 3/1990 | Hadersbeck et al. | 205/238 |
| 5,158,091 A | 10/1992 | Butterfield et al. | 128/672 |
| 5,245,293 A | 9/1993 | Runner | 324/663 |
| 5,572,115 A | 11/1996 | Strong et al. | 327/71.1 |
| 5,833,820 A | 11/1998 | Dubin | 204/212 |
| 6,004,440 A | * 12/1999 | Hanson et al. | 207/279 |
| 6,090,648 A | * 7/2000 | Reedy et al. | 438/155 |
| 6,384,610 B1 | 5/2002 | Wilson | 324/663 |

FOREIGN PATENT DOCUMENTS

| | | |
|---|---|---|
| DE | 8706256 | 8/1987 |
| DE | 4239495 | 5/1994 |
| DE | 19707788 | 7/1998 |
| FR | 2423776 | 12/1979 |
| FR | 2 732 465 A1 | 10/1996 |
| WO | 00/46593 | 8/2000 |

OTHER PUBLICATIONS

Database Derwent #002306158, WPI Acc.No. 1980–B2590C/198006, citing French Patent No. 2423776 published Dec. 21, 1979 (item D).

Database Derwent #009909585, WPI Acc. No. 1994–177291/199422, citing German Patent No. 4239495 published May 26, 1994 (item E).

Database Derwent #011946881, WPI Acc. No. 1998–363791/199832, citing German Patent No. 19707788 published Jul. 2, 1998 (item G).

Database Derwent, WPI Acc. No. 1996–457773/199646, citing French Patent No. 2 732 465, published Oct. 4, 1996 (see item F).

\* cited by examiner

*Primary Examiner*—N. Le
*Assistant Examiner*—Vincent Q. Nguyen
(74) *Attorney, Agent, or Firm*—Heller Ehrman White & McAuliffe

(57) ABSTRACT

A micro-electronic bond degradation sensor includes a sensor substrate having sensor circuitry and a sensor stud and a power stud extending therefrom. The sensor circuitry includes a voltage-to-current amplifier having an input coupled to sensor stud and an output coupled to the power stud. The voltage-to-current amplifier is operable to convert a voltage signal occurring along the sensor stud to a current signal output along the power stud.

3 Claims, 13 Drawing Sheets

MICRO-ELECTRONIC BOND DEGRADATION SENSOR AND METHOD OF MANUFACTURE

CROSS REFERENCE TO RELATED APPLICATIONS

This application is a continuing (divisional) application of U.S. Ser. No. 09/501,798 filed Feb. 8, 2000 by A. Wilson, now U.S. Pat. No. 6,384,610, which claims benefit of U.S. Provisional Application No. 60/119,166, entitled "Micro Electro-Mechanical Systems Adhesive Bond Degradation Sensors," filed Feb. 8, 1999, the contents of which are herein incorporated by reference in its entirety for all purposes.

BACKGROUND

This invention relates to devices and systems for detecting bond degradation and more particularly, to micro-electronic devices and systems for detecting degradation in an adhesive bond formed between two or more structures.

Bonded structures that are comprised of materials adhesively fixed together can provide relatively light weight with great strength. An adhesive material is typically applied to one or both of the materials, which are then pressed into contact. After the adhesive cures, the adhesive material holds the two materials together, without physically altering the state or condition of the respective materials. Bonded materials offers many advantages over traditional joined materials, which usually require drilling and riveting of plates with the consequent problems associated with increased stress at the rivet holes. Thus, the bonded materials do not loose any of their inherent strength or other features of the materials themselves. Bonded materials are extensively used, for example, in the aircraft industry for making aircraft wings, fuselage coverings, and other body structures.

A complete release of the bond between materials, called a disbanding, is unusual and, fortunately, is typically rather easy to detect. One problem with bonding technology is reliably detecting a loss of strength of the bonded structure, as opposed to a complete disbonding of parts of the structure. The lack of a test for partial bond degradation has (1) limited the application of bonded manufacture and repair technology, especially in critical components of air-frames; (2) meant that the current technology relies heavily on good bonding practice and procedures performed by trained technicians; (3) resulted in some aircraft in-service bonded repair failures with consequent impact damage with the separating bonded repair patch; and (4) resulted in unnecessary, and expensive, removal of old or suspect bonded repair patches for replacement with a new patch.

There is a great need for a reliable technique for monitoring the condition of bonded components in both military and civilian applications. The development of such techniques would lead to a greater confidence and hence wider application of bonding technology for manufacture and repair, more reliable condition-based maintenance of bonded structures, and improvements in bonding methods through the understanding gained from the use of degradation-sensitive sensors in the study of bond degradation mechanisms.

Macroscopic Fracture Mechanics Testing

Macroscopic examination of fractured surfaces has revealed that adhesive failure can occur at the adhesive bond interface between materials. Corrosion has been found to exist in the metal layers that are bonded together, under some conditions. Generally, fracture surfaces of specimens subjected to dry air show that failure occurs principally in the adhesive film itself. Fracture analysis of specimens tested in humid air, however, reveal large areas of adhesive failure at the bond interface, and also reveal evidence of corrosion in the bonded materials. This clearly demonstrates the need for a reliable metal interface sensor.

Common macroscopic testing methods that will be known to those skilled in the art include the "Boeing wedge test" (ASTM D3762-79, reapproved 1988) and the Constant Load Point Displacement Rate Test.

The Boeing wedge test is the standard test method for adhesive bonded surface durability of Aluminum (Al). The method simulates in a qualitative manner the forces and effects on any adhesive bond joint at a metal adhesive/primer interface. In the Boeing wedge test, one end of a double-cantilever beam (DCB) specimen is opened to a specified and constant crack opening displacement using a wedge. The elastic energy release rate depends on the crack length. The crack length typically cannot be measured accurately due to the uncertainty in locating the crack tip. Hence there is a need for a test that eliminates the need to measure the crack length.

The Constant Load Point Displacement Rate Test (CDRT) eliminates the need to measure the crack length. A bonded DCB specimen is opened at a constant load point displacement rate. The rate selected strongly influences the crack velocity. In humid air, the load-point displacement rate can be selected to drive the crack at a velocity that is either faster or slower than the rate of degradation of the bond ahead of the crack tip. The application of fracture mechanics to the CDRT leads to expressions for both the elastic energy release rate and crack velocity.

Unfortunately, none of the methods of fracture mechanics applied to the Boeing wedge test lead to well-defined parameters describing the rate of bond degradation. By contrast, the CDRT reveals the range in crack velocity where crack propagation undergoes a transition from un-degraded to degraded material. The transitional crack velocity is directly linked to the rate of bond degradation under apparent constant stress intensity at the crack tip. A limitation of the CDRT method is the long times typically required to obtain data from a range of load point displacement rates (up to 3 months).

Microscopic Investigation

Scanning Electron Microscopy (SEM) techniques have been used to investigate thin adhesive layers in adhesive/metal interfaces. The manner in which water degrades an adhesive bond is complex. It is believed that the processes of bond degradation involve the migration of water ahead of the crack tip, the decoupling of the adhesive or coupling agent from the oxide, and the hydration of oxide at the unprotected sites on the oxide surface. Models of the x-ray generation close to an interface, using Monte Carlo and finite element techniques, allow for the determination of thin layers on the interface and hence microscopic insight of the adhesive/metal interface. The SEM observations imply that the metal oxide is not being degraded by diffusion of water through the bulk oxide. Thus diffusion of water must be occurring either along the epoxy/metal oxide bond interface or within the epoxy. The macroscopic fracture mechanics tests would indicate that the diffusion of water is suspected to be along or very close to the interface.

Electrical impedance measurements from 10 Hz to 10 MHz have been performed on bonded specimens after different times of exposure to water. The results show that the metal-epoxy-metal bond initially behaves like a capacitor and then becomes more resistive at lower frequencies with longer exposure to water. This resistive behavior is due to the water penetrating the adhesive. Ions in the water oscillate under the influence of the alternating electric field. Above a certain frequency these ions will not be able to respond to the varying electric field, due to inertia, and the bond will once again appear capacitive. The impedance versus frequency dependence clearly differentiates between a bond with few voids and a bond with many voids after exposure to water. These measurements are also sensitive to the continuing degradation of the bond with ingress of water. Development of this technique could lead to a nondestructive technique for interrogating the integrity of adhesive bonds in the field.

Current NDE Systems for Bonded Components

Three conventional non-destructive evaluation (NDE) techniques are commonly used with adhesively bonded repairs. The three techniques are (1) x-ray tomography, (2) ultrasonics (including laser ultrasonics), and (3) infra-red imaging. All of these techniques are external to the bonded component. All are sensitive to gross dis-bonding and corrosion and, with infra-red imaging, can detect voids larger than approximately 1 square millimeter (mm) in a bond. None of the three techniques are sensitive to reduced bond strength when there is still good physical contact between the two bonded surfaces (the so called "kissing bond" problem). All of these NDE techniques require good access to the bonded region visually and/or manually. The x-ray systems often suffer from occupational health and safety considerations, since typical x-ray energies used are around 200 keV.

Honeywell Smart Sensor Technology

An electrochemical-based smart sensor system was developed by Honeywell Technology Center to provide early warning detection of corrosion related symptoms in hidden locations of aircraft structures. The Honeywell system, called "Smart Aircraft Fastener Evaluation (SAFE)" system, detects symptoms of extensive pH cycling and the presence of extensive moisture.

The SAFE system measures ionic activity in real time. The SAFE system uses a prototype Lawrence Livermore National Laboratory (LLNL) multi-element micro sensor array developed under the Smart Metallic Structures (SMS) program designed to sense a specific ionic phenomenon. Those skilled in the art will be familiar with the SAFE system and LLNL sensors.

The sensor system is packaged in Hi-Lok fasteners used to bolt aircraft skin together. Various methods for mounting the sensors in the fasteners have been used. Typically, a corrosive electrolyte solution is transported from between aircraft skin layers via a series of capillary channels located in the well of the fastener to an internally-located environmental chamber, where the LLNL sensor array can sense the effects and quantify early corrosion symptoms. Also used are designs with the sensors mounted in a shallow slot on the outside of the fastener.

The SAFE system provides sufficient corrosion monitoring capability in bolted areas. Unfortunately, corrosion detection using the SAFE system is often times only possible through empirical association without physical insight as to the cause of the bond degradation. Further disadvantageously, the hollow structure of the Hi-Lok fastener tends to lower the structural strength of the repaired structure. Further, the SAFE system sensors rely on the transport of ions through capillaries which can clog. Finally, the size of the sensors used in the SAFE system precludes their use in structural repairs requiring small bond lines such as aircraft and the like.

What is therefore needed is a bond degradation sensor which can detect the presence and rate of bond degradation in an adhesive bond line formed between two or more structures. Further needed is a bond degradation sensor of minimal size to permit the sensor's implementation within a thin adhesive bond line.

SUMMARY OF THE INVENTION

The present invention provides for a micro-electronic bond degradation sensor which is operable to detect the presence and rate of bond degradation in an adhesive bond line formed between two or more structures. The micro-electronic bond degradation sensor can be fabricated on the order of 20–100 $\mu m$ thick and can easily be embedded into very thin adhesive bond lines to provide accurate bond monitoring capability.

In one embodiment, the micro-electronic bond degradation sensor includes a sensor substrate having a sensor stud and a power stud extending therefrom. A sensor circuitry is additionally formed on the sensor substrate. The sensor circuitry includes a voltage-to-current amplifier having an input coupled to sensor stud and an output coupled to the power stud. The voltage-to-current amplifier is operable to convert a voltage signal occurring along the sensor stud to a current signal output along the power stud.

Other features and advantages of the present invention should be apparent from the following description of the preferred embodiment, which illustrates, by way of example, the principles of the invention.

DESCRIPTION OF THE SPECIFIC EMBODIMENTS

Outline of Contents

I. General Overview
II. Sensor Architecture
III. Sensor Monitoring System
IV. Sensor Fabrication
V. Applications

I. General Overview

Figure 1A:
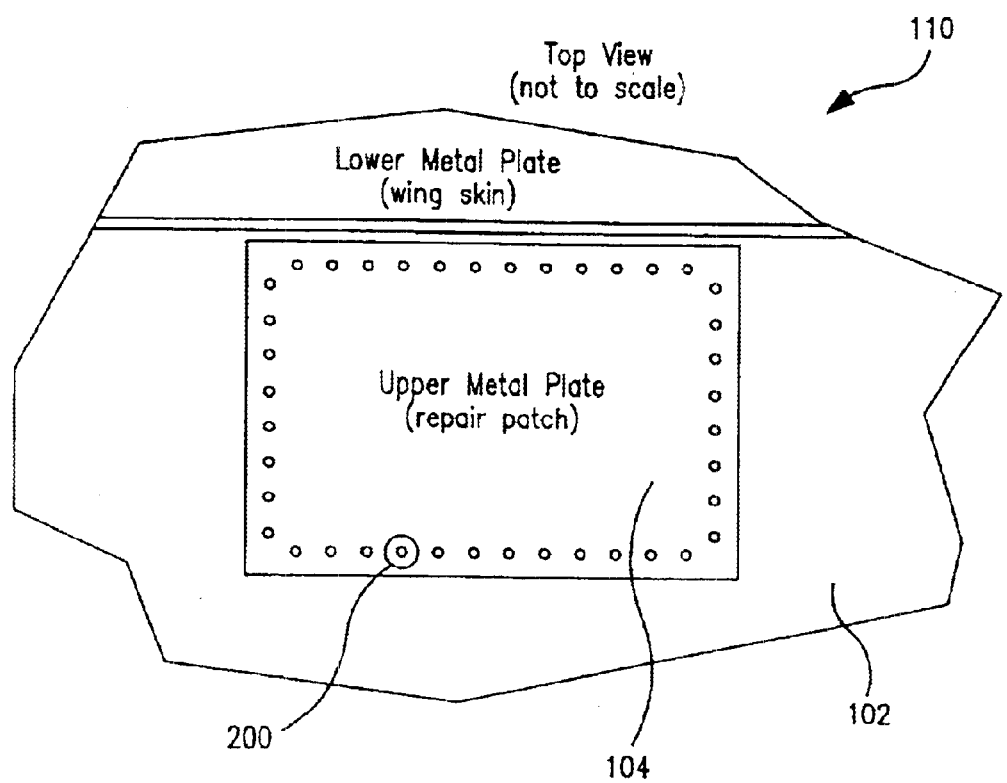
FIGS. 1A and 1B illustrate top and side views, respectively, of a bonded structure in accordance with one embodiment of the present invention.
Figure 1B:
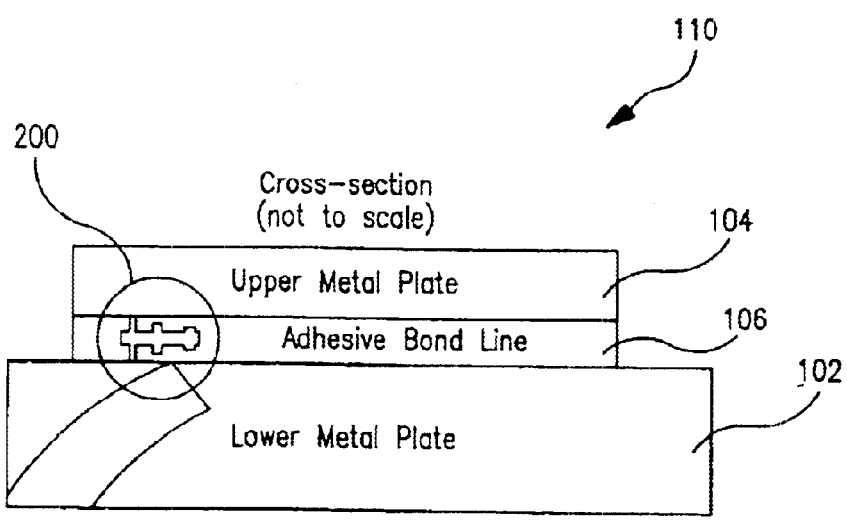

FIGS. 1A and 1B are top and side views, respectively, of a bonded structure 110 illustrated in accordance with one embodiment of the present invention. The bonded structure 110 includes a lower plate 102, a metallic wing span in the illustrated embodiment, which is repaired by an upper metal plate 104. The bonded structure 110 further includes one or more micro-electronic bond degradation sensors 200 (hereinafter sensor IC), which are preferably placed around the periphery of the upper plate 104. As shown in the side view of FIG. 1B, an adhesive bond line 106 provides attachment between the upper and lower plates 104 and 102, respectively. The adhesive bond line 106 may include an internal scrim to provide uniform thickness and electrical isolation between the upper and lower plates 104 and 102. The adhesive bond line 106 may be formed to any desired thickness, although in the illustrated embodiment in which the bonded structure 110 is an aircraft wing, the adhesive bond line is of a minimal thickness, preferably less than 500 $\mu$m, to preserve the structure's aerodynamic properties. In other embodiment in which the bond offset is not as critical, the adhesive bond layer 106 may exceed 500 $\mu$m.

In the embodiment in which both of the lower and upper plates 102 and 104 plates are composed of a conductive material, the conductive plates are used to communicate power and data signals to each sensor IC as will be further described below. In another embodiment in which one or both plates 102 and 104 are composed of a non-conductive medium, such as a composite material, power and/or data may be provided to each sensor IC 200 by a wire embedded in the adhesive bond line 106.

As appreciable to those skilled in the art, a variety of adhesive materials and compounds may be used to form the adhesive bond layer 106. In the illustrated embodiment in which a metal/metal bond is made, one possible class of compounds is a thermoset epoxy film adhesive, such as FM® 73 or FM® 300 available from Cytec Industries of West Paterson, N.J. These adhesives are commonly used in aircraft manufacture and repair, have been used in ship repair, and could be used in the automotive industry. Other adhesives may be used alternatively or in addition to the theromoset epoxy film adhesives.

II. Sensor Architecture

Figures 2A, 2B:
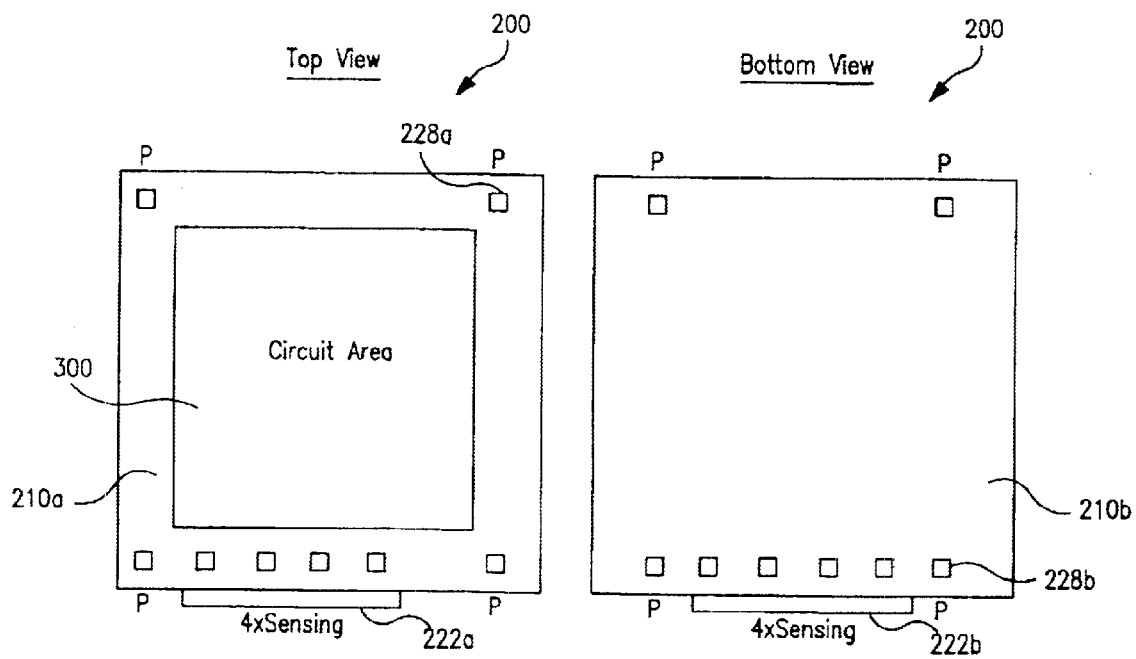
FIGS. 2A, 2B and 2C illustrate top, bottom and side layout views of the sensor IC in accordance with one embodiment of the present invention.
Figure 2C:
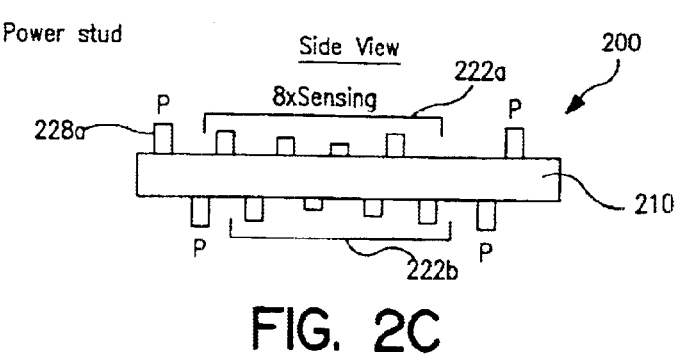

FIGS. 2A, 2B, and 2C illustrate top, bottom, and side views, respectively, of the sensor IC constructed in accordance with one embodiment of the present invention. FIG. 2A illustrates the top surface of the sensor substrate 210 which includes one or more top sensor studs 222a, one or more top power studs 228a, and sensor circuitry 300. The top sensor and power studs 222a and 228a extend substantially orthogonally from the substrate top surface 210a. The sensor circuitry 300 contains the chip's control and measurement circuitry, further described below.

FIG. 2B illustrates the bottom surface of the sensor IC 200. In this embodiment, the bottom surface includes one or more bottom sensor studs 222b and one or more bottom power studs 228b, each extending substantially orthogonally from the bottom surface. The substrate's bottom surface 210b may also include a circuit area alternatively or in addition to the circuit area 300 formed along the substrate's top surface.

FIG. 2C illustrates a side view of the sensor IC 200. As can be seen, the top and bottom power studs 228 extend the farthest from the sensor substrate 210. The top and bottom sensor studs 222 are configured to extend various distances from the sensor substrate 210. In the preferred embodiment, the sensor substrate 210 has a thickness dimension (or height) which is preferably less than the thickness of the adhesive bond line 106. Further, the sensor studs 222 are formed at varying heights such that at least one does not contact the opposing metal plate 102 or 104.

Once the sensor IC 200 is embedded into the adhesive bond line 106, the condition of the adhesive bond/metal interface can be assessed by monitoring one or more electrical parameter between one or more non-contacting sensor studs 222 and the opposing plate 102 or 104. In a specific embodiment, the voltage between a non-contacting sensor stud and the opposing plate is monitored to detect the presence and rate of bond degradation.

In an exemplary embodiment, the sensor substrate is a complementary metal oxide semiconductor (CMOS) die measuring approximately 1 mm(l)×1 mm(w)×25 $\mu$m(h), the fabrication processes of which will be further described below. Further preferably, the power and sensor studs 222 and 228 are composed of copper-plated aluminum and extend 15 $\mu$m to 40 $\mu$m from the top and bottom surfaces 210a and 210b, respectively. Those of skill in the art will appreciate that substrates and studs of varying materials and/or dimensions may be used in alternative embodiments.

Figure 3A:
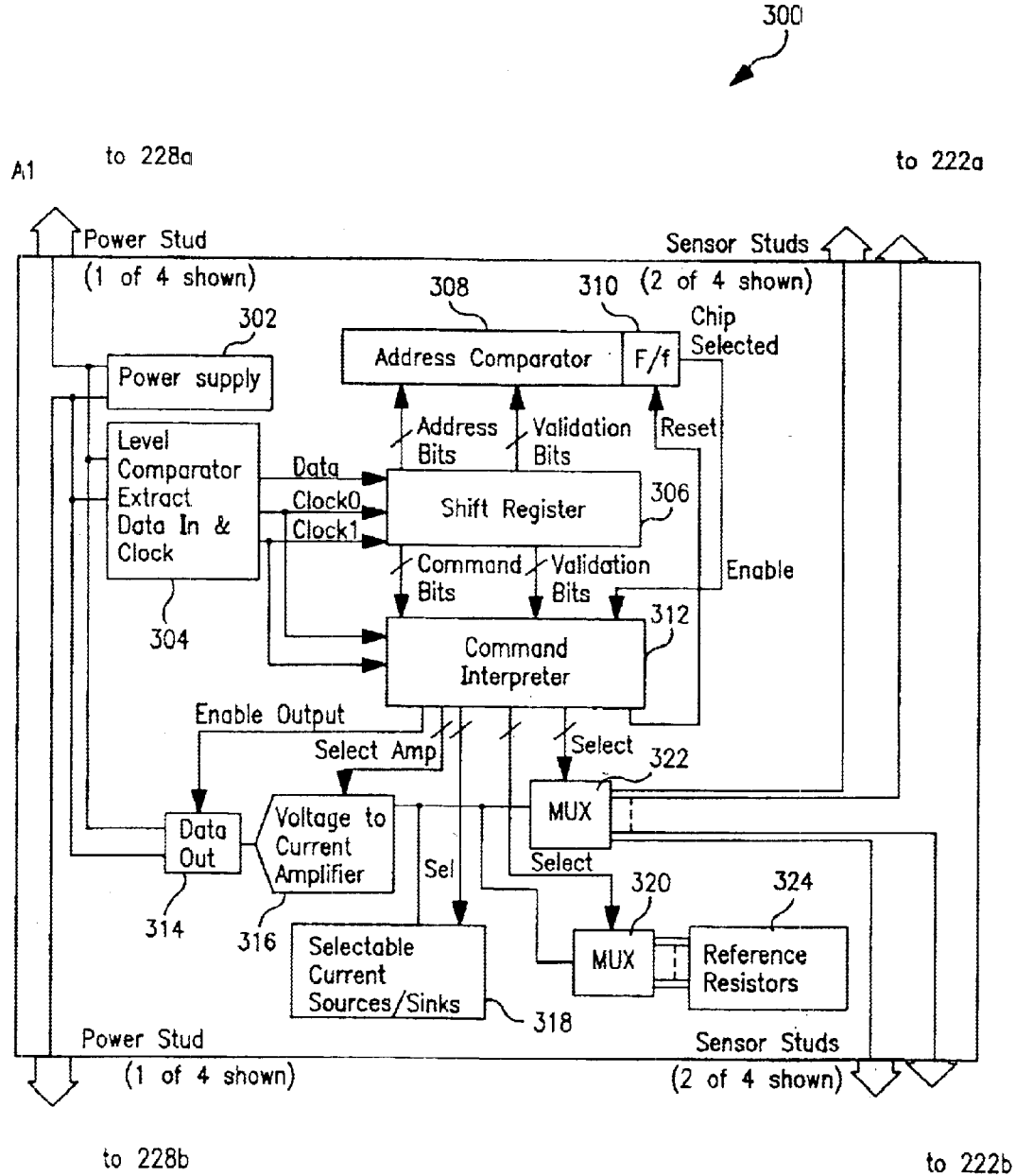
FIG. 3A illustrates a schematic of the sensor circuitry in accordance with one embodiment of the present invention.

FIG. 3A illustrates a schematic of the sensor circuitry 300 in accordance with one embodiment of the present invention. As illustrated, the sensor circuitry 300 includes a power supply 302, a data extraction circuit 304, a shift register 306, an address comparator 308, a chip select register 310, a command interpreter 312, a data output mux 314, two voltage to current amplifiers 316, one or more selectable current sources/sinks 318, a first analog multiplexer 320, a second analog multiplexer 322 and one or more reference resistors 324. Of course, other circuitry may be implemented alternatively or in addition to those components illustrated.

A power supply 302 is coupled to the power studs 228 and is operable to provide one or more sources of regulated power to the sensor circuitry 300. The power supply 302 may include voltage regulation circuitry to provide stable internal voltages over varying input voltage levels. In some applications, the power supply circuit is not required.

A data extraction circuit 304 has an input coupled to the power studs 228. As described in further detail below, clock and data signals are combined with a power signal to form a multiplexed signal which is communicated to the sensor IC 200 via the via the power stud 228. The data extraction circuit 304 extracts the clock and data signals and routes these signals to the control and measurement circuitry.

Figure 3B:
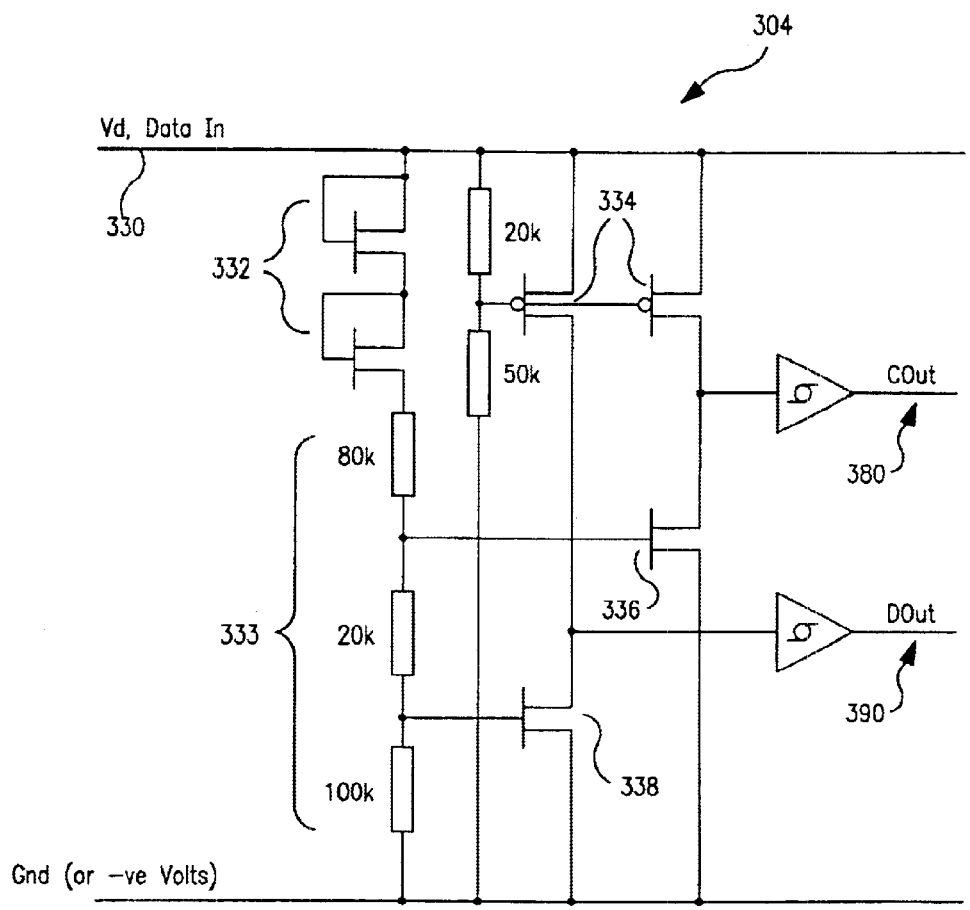
FIG. 3B illustrates one embodiment of the front end of data extraction circuitry in accordance with one embodiment of the present invention.
Figure 3C:
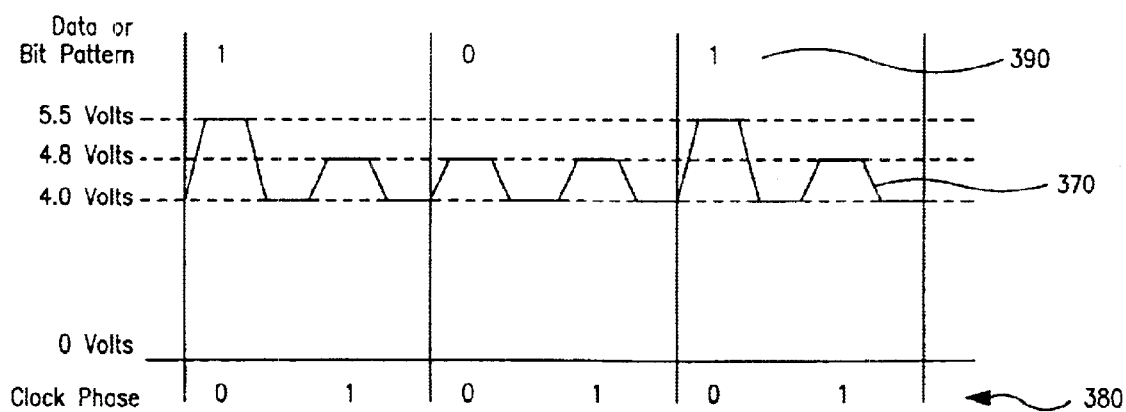
FIG. 3C illustrates an exemplary input waveform, an output clock phase signal 380 and a data output signal generated in accordance with one embodiment of the present invention.

FIG. 3B illustrates one embodiment of the front end of the data extraction circuitry 304. FIG. 3C illustrates an exemplary input waveform 370, an output clock phase signal 380 and a data output signal 390 for the data extractor circuit 304.

During operation, a data signal 370 is provided along the input 330 as a modulated power supply voltage. The modulated power supply voltage is detected by MOS transistors 334, 336 and 338 which in the preferred embodiment are referenced to the ground. The MOS transistors 332 provide a roughly constant voltage reduction to the resistor divider network 333. The MOS transistors 336 and 338 in conjunction with the resistor divider network 333 are operable to conduct at different power supply input voltage levels. The data extraction circuit 304 operates to convert a high voltage level (5.5 V in the illustrated embodiment of FIG. 3C) to a phase0 clock signal and high (1) bit. The data extraction circuit 304 converts a low voltage level (4.8 V in the illustrated embodiment of FIG. 3C) to a phase0 clock signal and low (0) bit or a phase1 clock signal if a phase0 clock signal immediately preceded the low voltage level. A single data bit consists of two clock signals, phase0 and phase1, as illustrated in FIG. 3C. Data is input during clock phase0 by taking the power supply voltage 330 to either a high voltage level or low voltage level 370 corresponding to a high data bit or low data bit respectively. The clock phase1 signal is a low voltage. Additional standard logic circuits and latches (not shown) generate the two phase non-overlapping clock and a high or low data signal for the rest of the CMOS circuitry, the clock0, clock1 and data signals from 304 in FIG. 3A. In this implementation, the phases of the internal sensor clock and external data input are synchronized by forcing the sensor circuitry to generate a clock phase0 whenever the data input is high.

In the preferred embodiment, the sensor circuitry 300 further includes components to perform: (a) address decoding to allow selection of a sensor IC 200; (b) actions determined by the commands issued to the sensor IC 200; (c) measurement of the sensor studs 222, and (d) data output.

Address Decoding and Command Data

Twelve-bit data words are used in this implementation although data words of longer or shorter bit lengths may be used in alternative embodiments. Data is input to a 12-bit Shift Register (SR) 306 which is clocked using the non-overlapping, two phase dual clock signals, clock0 and clock1. The first two data bits and the last data bit are used to determine that the SR 306 has a valid address or command. The middle nine bits contain the address or command function.

In the preferred embodiment, the input data is processed in three ways depending upon the state of the sensor IC. In the first operational state, a valid address is received and the remaining nine data bits define the address of the selected sensor IC. In the preferred embodiment, each sensor IC has a unique selection of the data and negated data outputs of the SR 306 hard wired to the address comparator 308, which consists of a set of NAND gates, to determine whether the particular sensor has been addressed. This hardwiring is determined by the connection patterning in the final metal layer of the integrated circuit. When the sensor IC is selected an internal latch circuit 310 records this and through the command interpreter 312 resets the SR 306 ready for another data word.

In a second operational state, the sensor IC has previously received a valid address word to select the sensor, indicated by the latch 310 being set, and subsequently receives a valid command word. In this state, the command remains in the SR 306 and the nine command bits are presented to the command interpreter 312. The data bits presented to the command interpreter 312 to determine the action of the sensors IC chip.

In a third operational state, the sensor IC is selected and the command received into the command interpreter 312 is an instruction to read a sensor stud 222 or internal reference resistor 324. In this state, receipt of low data bits toggles the data output mux 314 on and off. Receipt of a high data bit resets the command interpreter 312 to a ready state to accept a new command.

Sensor Control

The command interpreter 312 control circuitry is a set of static logic gates and latches which perform the following functions: (a) selection of either an internal reference resistor 324 or a sensor stud 222 to monitor; (b) selection of the current 318 to use for the measurement; (c) selection of the measurement amplifier 316 to be used and (d) toggling of the sensor output 314 onto the power lines. The command interpreter 312 activates one or both multiplexers 320 or 322 to connect the current sources/sinks 318 to the reference resistors 324 or the measurement studs 222, respectively. Connection of the current sources/sinks 318 to reference resistors 324 produces one or more reference voltages to the input of the voltage-to-current amplifier 316 for calibrating the sensor IC. Connection of the current source/sink 318 to the sensor stud 222 provides a measurement voltage to the input of the voltage-to-current amplifier 316. The data output mux 314 switches the corresponding measurement current to one or both of the power studs 228a or 228b. In the preferred embodiment, multiplexers 320, 322 and 314 are CMOS analog switches.

Sensor Measurement

The condition of the adhesive bond/metal interface may be monitored by measuring one or more electrical parameters between one or more non-contacting sensor studs and the opposing plate 102 or 104. In an exemplary embodiment, a direct current (dc) voltage is measured. Those of skill in the art will appreciate that other dc measurements as well as alternating current (ac) measurements may be made alternatively or in addition to the dc voltage measurement.

Responsive to a control signal from the command interpreter 312, a mux 318 selects a constant current source/sink to supply or pull current from the sensor stud 222. The sunk/supplied current develops produces a voltage between the sensor stud 222 and the opposing plate 102 or 104. The mux 322, responsive to a control signal output from the command interpreter 312, routes the sensor stud voltage to the input of the voltage-to-current amplifier 316. The voltage-to-current amplifier 316 converts the sensed voltage to a modulating current signal. In the preferred embodiment, the voltage measurements are made periodically, each over a short duration in order to preserve power. In alternative embodiments, the timing and duration of the measurement may vary.

In illustrated embodiment, eight sensor studs are provided, four on each side of the sensor IC 200. The sensor studs 222 are formed at different heights to ensure that at least one sensor does not contact the metal plate which would prevent an accurate bond degradation measurement. The sensor circuit 300 includes four selectable current sources and four selectable current sinks 318 to provide a wider dynamic range for the conductivity measurements.

Additionally, four reference resistors 324 are included in the sensor circuitry 300 and are operable to provide a reference voltage to the voltage-to-current amplifiers for an internal calibration.

Further preferably, two voltage-to-current amplifiers 316 are provided in order to allow measurement over the entire power supply voltage range. A first voltage-to-current amplifiers is attached to ground/reference system potential (228a in the illustrated embodiment) and a second voltage-to-current amplifier referenced to the power supply (228b in the illustrated embodiment). In this embodiment, the command interpreter 312 supplies a control signal to select between the amplifiers. In an alternative embodiment, one or both of the voltage-to-current amplifiers may be replaced with an analog-to-digital converter.

Data Output

Responsive to a control signal supplied from the command interpreter 312, the data output mux 314 routes the modulated current signal to either the top or bottom power studs 228a or 228b, respectively. In the illustrated embodiment in which the upper plate 104 is the non-reference or signal plate, the data output mux 314 routes the modulated current signal to the top power stud 228a. The modulating current signal propagates along the upper plate 104 to an external interface 430 and connecting computer system 470, further illustrated in FIG. 4A and described below.

In the preferred embodiment, the modulated current signal can be toggled on and off by successive low data clock pulses input to the sensor IC 200. This allows the current sensing circuitry to perform more accurate measurement of low level signals by offsetting the no-signal current. If an analog-to-digital converter is used in place of a voltage-to-current amplifier 316, a current sink output could be used to transmit high and low data bits.

As described above, the sensor IC 200 is operable to measure the voltage developed between a sensor stud 222 and the opposing plate when a constant current is provided to the sensor stud 222. The sensor IC is further operable to perform other measurements either alternatively or in combination with the described measurement technique in order to assess the state of the bond In an alternative measurement technique, the sensor voltage potential may be monitored with a zero current supply. If it is assumed that the Cu generally operates as a reference electrode (i.e., not being attacked by the local environment) then the voltage is a quantitative measurement of the amount of degradation. However, the signal is lower than that measured by the passing a constant current between a sensing stud 222 and one of the metal plates. For example, for Al corrosion the starting potential is around −1V (corresponding to no corrosion) dropping to −0.7V when it is heavily corroded.

Secondly, the conductivity may be measured with an ac signal, preferably at a frequency of greater than 1 KHz. This will tend to mitigate possible problems associated with the polarization resistance on the Cu and Al surfaces, giving a truer measurement of conductivity between the sensors. The potential that is being measured in the sensor stud includes that due to the resistance at the Al and Cu surfaces and that in the epoxy. With long measurement times (greater than milliseconds) a polarization resistance builds up around the Al and Cu due to the accumulation or depletion of ions close to the metal surface. AC signal measurements may mitigate these problems. Gold electrodes which are more stable than Cu electrodes, and would act as true reference electrodes, could be used for the above measurements.

The CMOS layout may be designed using any standard CMOS software design package (for example Tanner EDA L-Edit® software). Tanner EDA T-Spice® software (or any other implementation of SPICE circuit simulation software) can be used to evaluate and emulate the performance of these CMOS circuits.

III. Sensor Monitoring System

Figure 4A:
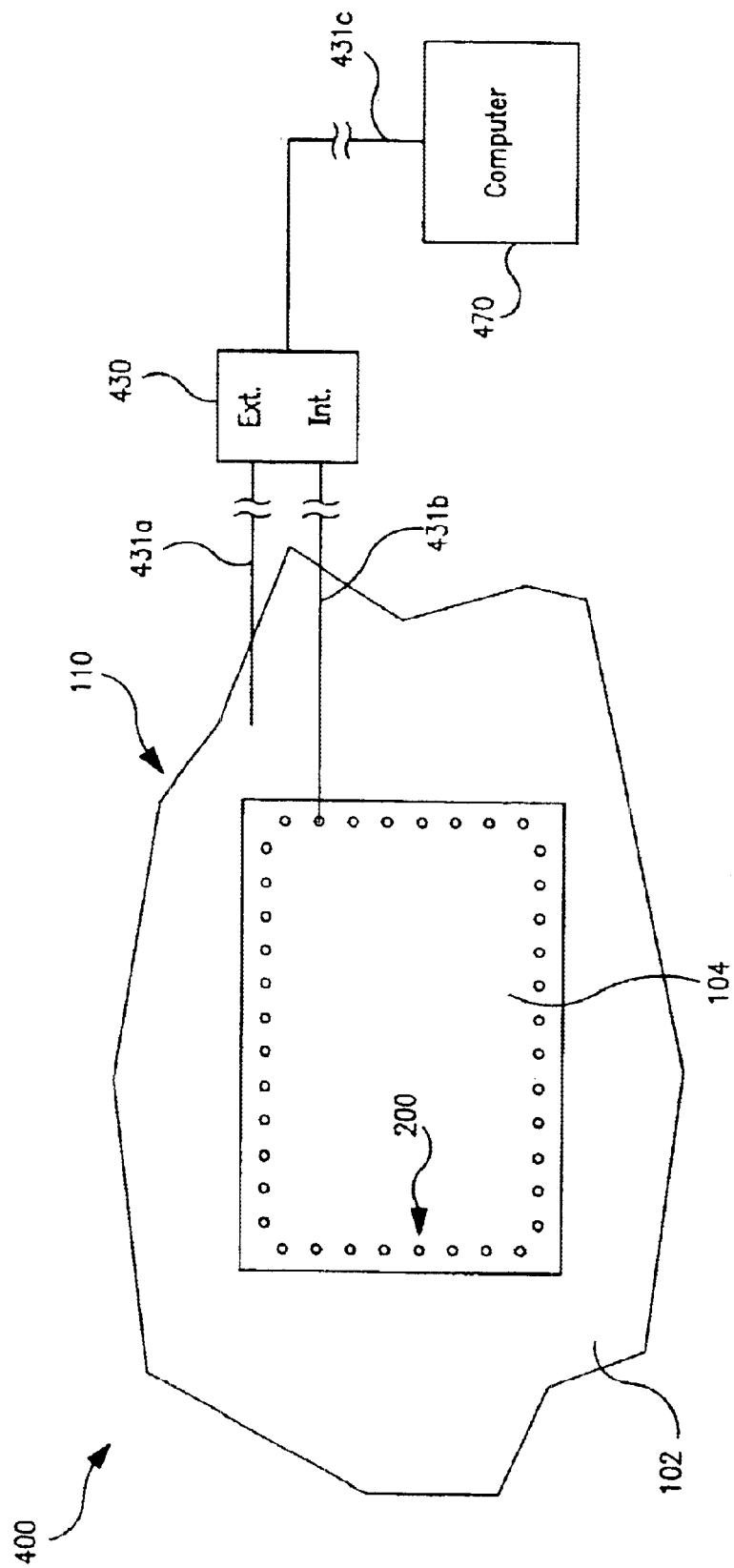
FIG. 4A illustrates a monitoring system in accordance with one embodiment of the present invention.

FIG. 4A illustrates a sensor monitoring system 400 in accordance with one embodiment of the present invention. As illustrated, the sensor monitoring system 400 includes the bonded structure 110, an external interface 430, and a computer system 460 470. The bonded structure 110 includes the above-described upper plate 104 which is adhesively bonded to the lower plate 102. One or more sensor ICs 200 are preferably located around the periphery of the upper plate 102, although in an alternative embodiment, the sensor ICs 200 may be located in a different or random pattern throughout the bonded area.

The external interface 430 is coupled to the bonded structure 110 via two lines: a reference (or 0V) line 431a coupled to the lower plate 102 and a power/communication line 431b coupled to the upper plate 104. In the illustrated embodiment, the lower plate is the frame of the aircraft and thus defines the reference potential of the structure. In an alternative embodiment in which the upper plate constitutes the reference (for instance, when a repair is made underneath the wing) the lines 431a and 431b would be reversed.

The external interface 430 is further coupled to the computer system 460 via a line 431c which is preferably a bus for communicating data, control, power and/or other signals between the external interface unit 430 and the computer 470. The computer may be a conventional computer machine, further described in FIGS. 4C and 4D.

Figure 4B:
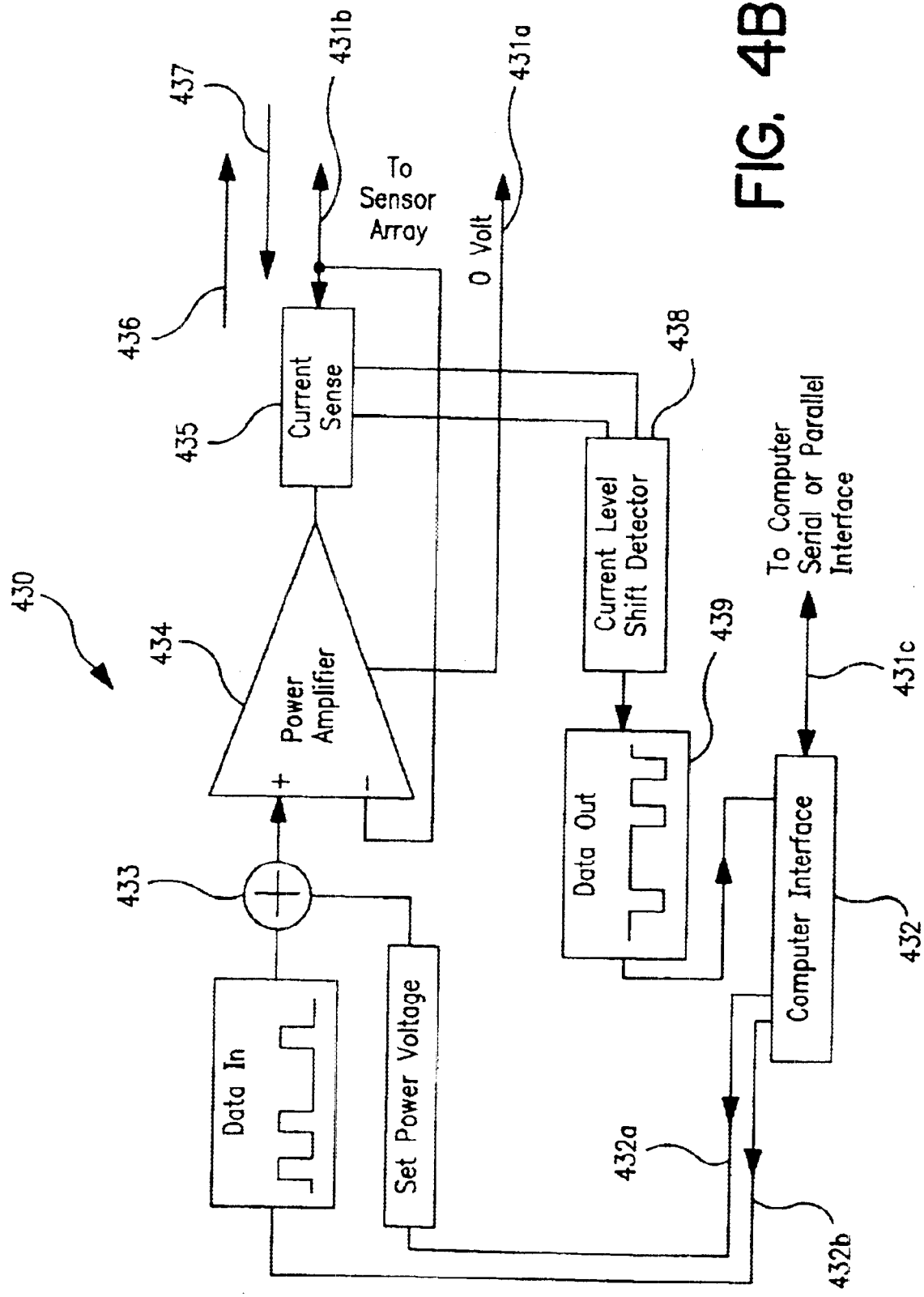
FIG. 4B illustrates one embodiment of the external interface shown in FIG. 4A.

FIG. 4B illustrates a schematic block diagram of the external interface 430 in accordance with one embodiment of the present invention. The external interface 430 includes a computer interface 432, a summer 433, a power amplifier 434, a current sensor 435, and a current level shift detector 438.

During operation, the external interface 430 receives, via the bus line 431c, a power signal 432a and a data signal 432b from the computer system 460. The power signal 432a is provided to power up to all of the sensor ICs 200 located in the bonded structure 110. The data signal is provided to control and/or communicate with one, several or all of the sensor ICs 200 within the bonded structure 110. The power and data signals 432 are multiplexed together using the summer 433 and the multiplexed signal is amplified by the power amplifier 434. A current sensor 435 coupled at the output of the power amplifier provides little or not effect to the output multiplexed signal. In the preferred embodiment, the inverting input on the power amplifier is coupled to the power amplifier output in order to provide feedback control. A coupler or other device may be coupled along the feedback path to sense the amplitude, phase, frequency and/or other signal parameters of the output multiplexed signal 436 in order to better control the signal's characteristics.

The output multiplexed signal 436 corresponds to the input waveform 370 illustrated in FIG. 3C. Specifically, the output multiplexed signal 436 has a DC power component operable to power the sensor ICs 200 and a modulating data component operable to provide communications and control to the sensor ICs as described above. The output multiplexed signal 436 is provided to the upper plate 102 of the bonded structure via line 431b and a ground or other reference signal is provided the lower plate 104 of the bonded structure 104 via line 431a. Preferably, the lower plate 102, the external interface unit 430 and the computer system 460 are all tied to the same ground or other reference signal. In severe electrical environments an optically isolated computer interface 432 could be used and the external interface 430 could use batteries or an independent or isolated power supply.

The external interface 430 is further operable to receive a sensor IC signal 437 which, in the illustrated embodiment, consists of a modulating current signal, as described above. The current sensor 435 is coupled to sensor's power studs 228 via the upper plate 102 and the power/communication line 43b, and is operable to detect the modulating current signal. The current sensor is polled during times at which no multiplexed signals 436 are being output. The current sensor 435 is coupled to a current level shift detector 438 which operates to convert the modulating current signal to a digital output 439 for communication to the computer system 460 for analysis.

Figure 4C:
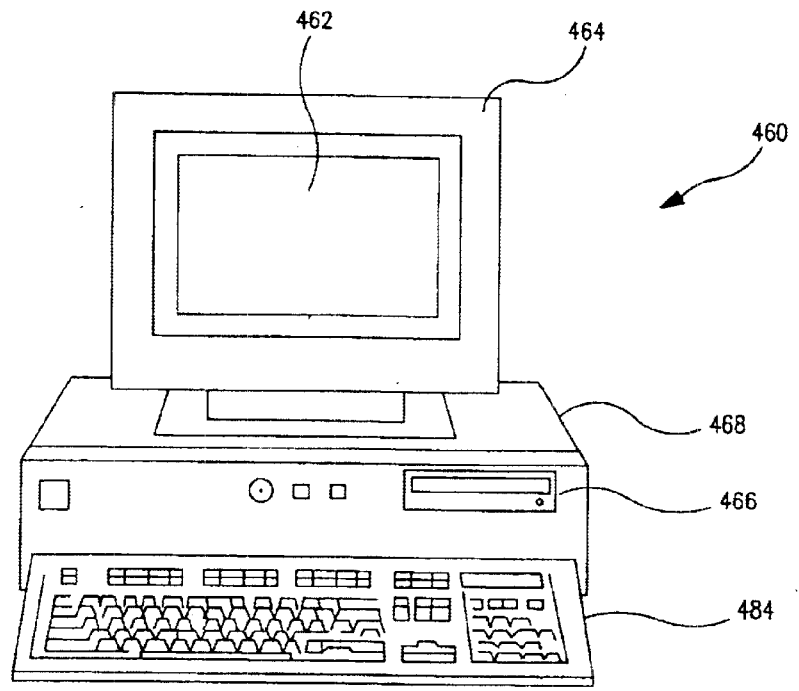
FIG. 4C illustrates one embodiment of the computer system shown in FIG. 4A.

FIG. 4C illustrates one embodiment of the computer system 460 configured in accordance with one embodiment of the present invention. The computer system 460 includes a monitor 464, screen 462, cabinet 468 and a keyboard 484. A mouse (not shown) may also be included for providing additional input/output commands. Cabinet 468 houses a mass storage device 466 such as a hard drive operable to store data and computer readable instructions which may be utilized to execute the processes of the present invention. Alternatively the mass storage device 466 may be a fixed or removable disk drive such as a floppy drive, a DVD or CD read only drive, or a writeable or re-writable drive. In this instance, the disk drive 466 accepts a matching disk (not shown) which stores the aforementioned data and computer-readable instructions. Cabinet 468 also houses familiar computer components (not shown) such as a central processor, memory, and the like.

Figure 4D:
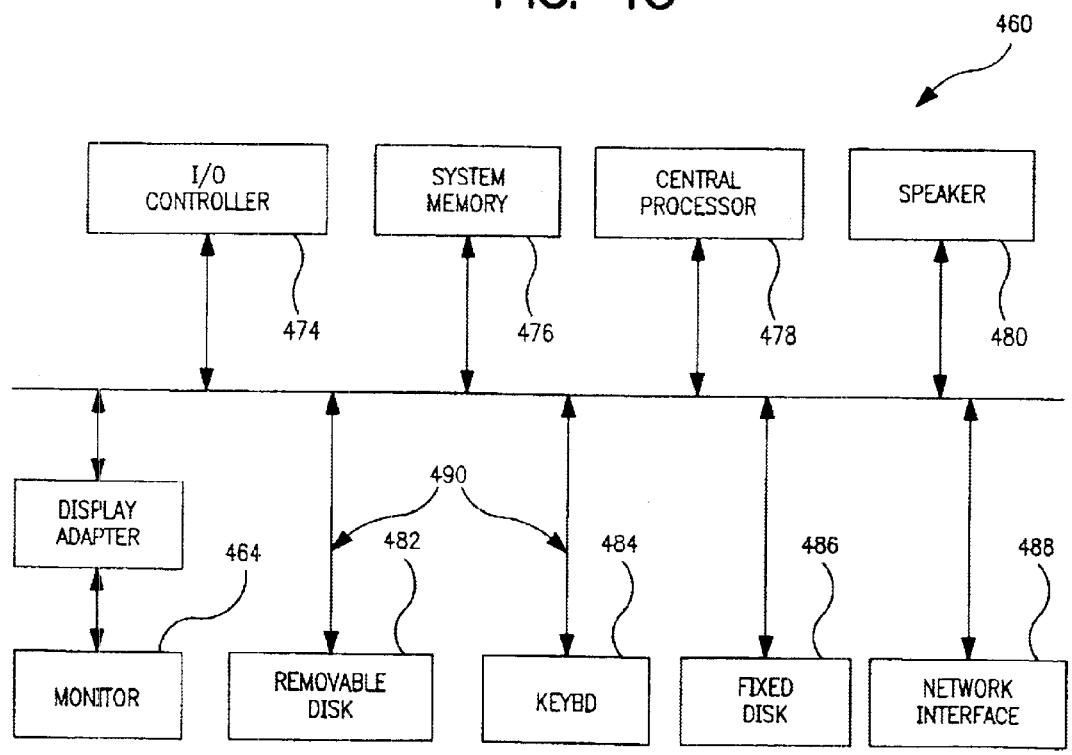
FIG. 4D illustrates the internal architecture of the computer system shown in FIG. 4C.

FIG. 4D illustrates the internal architecture of the computer system shown in FIG. 4C. The computer system 460 includes familiar subsystems such as one or more I/O controllers 474, system memory 476, a central processor 478, one or more speakers 480, a removable disk 482, keyboard 484, fixed disk 486, and a network interface 488. Additional subsystems may be included as well. For example, the computer system may include a second processor (e.g., a math co-processor). Arrows such as 490 represent signal flow and bus architecture, although those of skill in the art will appreciate that other bus architectures are possible as well. For example, a dedicated bus may be established between the system memory 476 (SDRAM in one embodiment) and the central processor 478 (a Pentium™ III in one embodiment). Other bus architectures will be apparent to those skilled in the art.

IV. Sensor Fabrication

In the preferred embodiment, the sensor IC is fabricated using a CMOS process using Silicon-On-Insulator (SOI) wafers, known in the art. The SOI wafers typically consist of a device layer (typically 15 $\mu$m thick) formed on top of a buried thick oxide layer (0.5–3.0 $\mu$m available from suppliers) formed on top of a Si handle wafer (typically 500 $\mu$m).

Figure 5A:
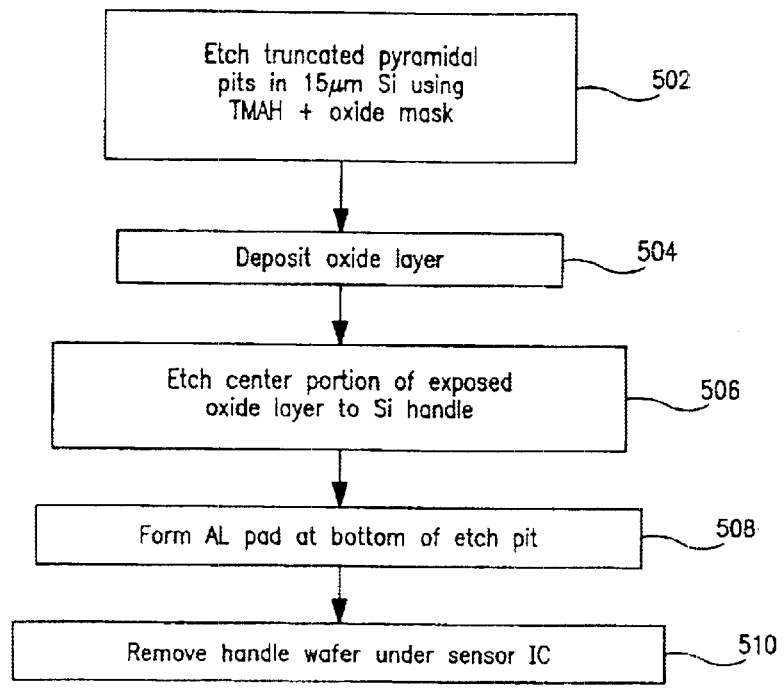
FIG. 5A is a flowchart illustrating the process by which aluminum pads are fabricated on the bottom surface of the sensor IC formed on a silicon on insulator wafer in accordance with one embodiment of the present invention.
Figure 5B:
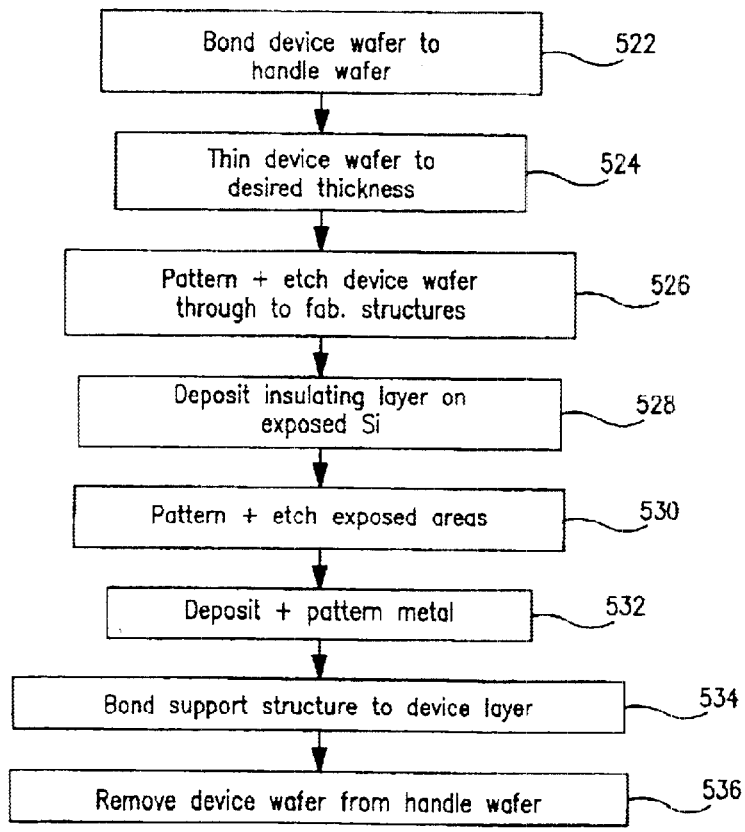
FIG. 5B is a flowchart illustrating the process by which aluminum pads are fabricated on the bottom surface of an sensor IC formed on a standard silicon wafer in accordance with one embodiment of the present invention.

Fabrication of all of the sensor circuitry 300 and the top side Al pads may be performed using a conventional CMOS processes. However, formation of the bottom side Al pads are not conventional processes. FIGS. 5A and 5B illustrate two processes by which bottom side Al pads are formed in accordance with the present invention.

FIG. 5A is illustrates a bottom side Al pad formation process for SOI sensors. Initially at 502, truncated pyramidal pits in the device layer are etched. Preferably, the pits are etched using Ammonium TetraMethyl-Hydroxide (TMAH) and an oxide mask layer. Next at 504, an oxide (or nitride) layer is deposited (or grown) to electrically isolate the exposed Si in the etched pits. In the preferred embodiment, the oxide (or nitride) layer is deposited on the top surface of the device layer, on the bottom surface of the Si handle and on the insides of the etched pit.

Subsequently at 506, a center portion of the exposed buried thick oxide layer is etched down to the Si handle. Next at 508, an Al pad at the bottom of the etch pit is formed which is electrically connected to circuits on the top of the 15 $\mu$m device layer. This process may be achieved with a combination of standard thickness (and extra thick, if necessary) Al deposition and patterning. In an alternative embodiment, Cu may be deposited at the bottom of the etched pits. Next, Al is deposited over the Cu to make contact between the Cu and the Al wiring in the CMOS section of the sensor. A Cu diffusion barrier may be necessary since the wafer is held at an elevated temperature for the final protective glass deposition fabrication step.

Subsequently at 510, the 500 $\mu$m handle wafer is removed underneath the sensor IC. This operation is performed in the preferred embodiment with an extended, single sided etch using TMAH doped with Si (Si doped TMAH does not attack Al). At the end of this process, the Al deposited in the bottom of the truncated pyramidal pits will be exposed to form the pads for electroplating on the bottom of the sensor IC. If a Cu layer is deposited in 508 rather than Al, undoped TMAH can be used since attack of Cu by TMAH is low. The wafer will now consist of a square mesh of thick Si ribs supporting the thin chip sensors.

The formation of the pits in the top surface of the wafer may have an impact on the photo-lithographic processing. In this case, a thicker coating resist can be used during the fabrication process.

Due to the ease with which backside Al pads are formed on sensor ICs fabricated on SOI wafers, SOI wafers are the preferred substrate used. However, SOI wafers are more expensive compared to standard silicon (Si) wafers. Therefore, it is advantageous to present a backside Al pad formation process suitable for standard Si wafers.

FIG. 5B illustrates a backside Al pad formation process for sensor ICs formed on a standard Si wafer. Initially at 522, the top side of the Si device wafer, which has undergone all of the required CMOS processing and sensor fabrication, is bonded to a handle wafer. In the preferred embodiment, the bonding method is compatible with all etchants and processing conditions in the following processes.

Next at 524, the bottom side of the Si device wafer is mechanically-chemically thinned to the required thickness. Subsequently at 526, the exposed bottom surface of the Si device wafer is coated, patterned and etched through to make via holes to previously fabricated structures on the top side of the Si device wafer. Next at 528, an insulating layer is deposited on the exposed bottom surface of the Si device wafer. At 530, the insulating layer is patterned and etched to expose the areas which form the electrical connection to the sensor circuitry 300.

Next at 532, metal, (aluminum in the preferred embodiment) is deposited and patterned on the device wafer. This metal forms both (1) the via connections from the bottom surface to the CMOS circuits on the top of the sensor IC and (2) the pads for electroplating on the bottom of the sensor IC. At 534, a support structure is bonded to the device layer which leaves all plating pads exposed. The support structure is preferred since electroplating is performed on both sides of the wafer. The support structure preferably remains in place during removal of the handle wafer at 536. Once the handle wafer has been removed at 536, the sensor and power studs are formed, two processes of which are further described in FIGS. 7A and 7B below.

The power and sensor studs are preferably fabricated after all of the CMOS processing has been completed but prior to wafer dicing. For double-sided sensor ICs, the bulk thinning of the sensor ICs has also been performed. In this embodiment, the sensor and power studs consist of Cu studs electroplated onto exposed Al pads on the Si CMOS wafer. Those of skill in the art will appreciate that other metals could be electroplated as sensor studs.

The Cu electroplating current/area is preferably lower for studs that are shorter. In the preferred embodiment, electroplating is performed on whole wafers for efficient, low cost and volume production. This process may be achieved in the following ways: (a) using an electroplating bus bar system that supplies different currents to the different plating pads over the whole wafer and/or (b) using on chip CMOS current sources which will only need power and an optional enable signal to be supplied over the whole wafer. Either or both of these approaches may utilize an external electrical connection to the wafer while it is immersed in the electroplating bath.

Figure 6A:
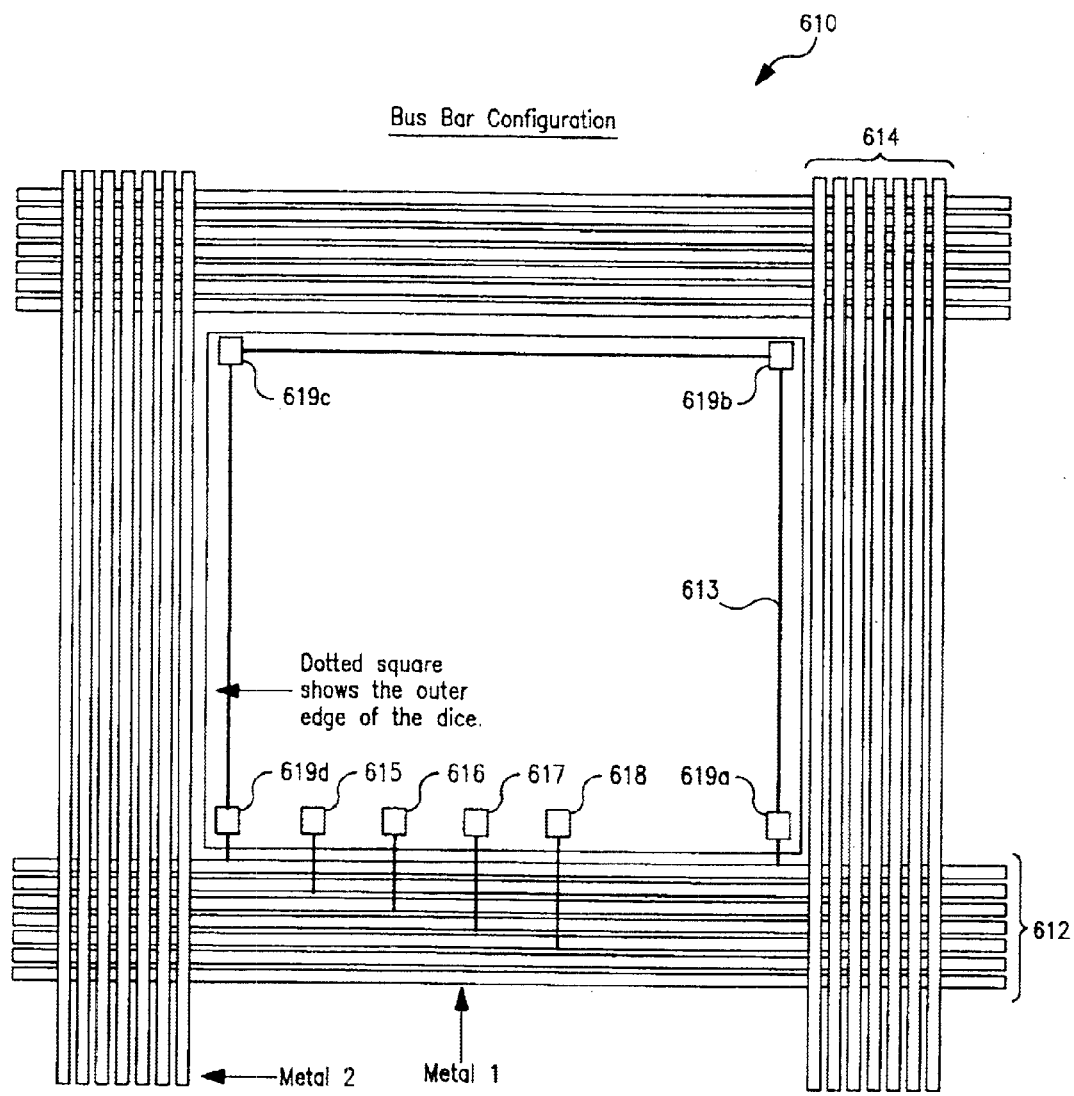
FIG. 6A illustrates a top view of an electroplating bus constructed in accordance with the one embodiment of the present invention.

FIG. 6A illustrates a top view of a electroplating bus 610 constructed in accordance with the one embodiment of the present invention. In this embodiment, the bus 610 includes seven first metal layers 612 and seven second metal layers 614 located around the periphery of a sensor IC 200. A second electroplating bus 613 is also formed just inside the periphery of the sensor IC 200 and interconnects the points at which the power studs are to be formed.

Connected to seven first metal layers are five plating pads 615, 616, 617, and 618. Plating pads 615–618 are provided to form each of the four sensor studs 222a illustrated in FIG. 2C. By providing a separate plating connector to each sensor stud, each sensor stud may be formed at different dimensions. Plating pads 619a–d are interconnected via the second electroplating bus 613 and are provided to form power studs 228a, each of equal dimensions.

Figure 6B:
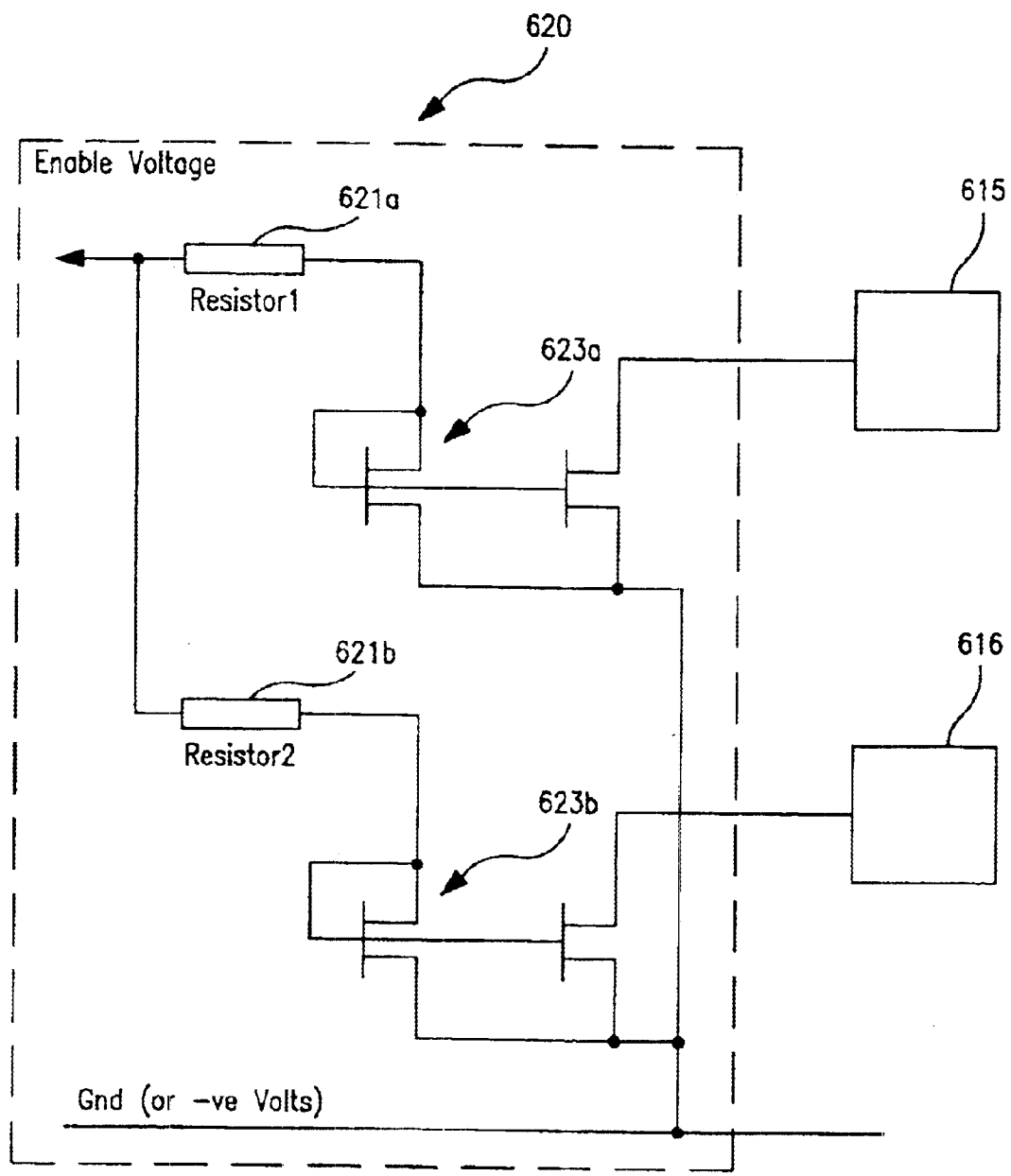
FIG. 6B illustrates one embodiment of a electroplating control circuit configured in accordance with the present invention.

FIG. 6B illustrates one embodiment of an on-wafer electroplating control circuit 620 configured in accordance with the present invention. The electroplating control circuit 620 is used to control the formation process of the sensor and power studs formed on the connecting plating pads 615–619. The on-wafer electroplating control circuit 620 includes a first resistor 621a coupled to a first current driver 623a and a second resistor 621b coupled to a second current driver 623b. The first and second resistors are connect at a common node where an input enable voltage may be applied. In the illustrated embodiment, the first and second current drivers 632a and 623b are coupled to the plating pads 615 and 616, respectively. In other embodiments, the on-wafer electroplating control circuit 620 may supply one, three or more plating pads 615–619. Each of the current drivers 623 are realized as a two device FET current mirror. Those of skill in the art will appreciate that other non-FET transistor architectures or circuit configurations may be used in alternative embodiments.

During operation, an enabling voltage is applied to the input of the control circuit 620 and a resulting current is delivered to the plating pads 615 and 616. The amount of electroplating current delivered to each plating pad (and accordingly the resulting element's dimensions) is determined by the value of the connecting resistor and the connecting current driver. In the illustrated embodiment, the two plating pads 615 and 616 may be supplied different electroplating currents using the same enabling voltage if the resistance values 621a and 621b are selected to be different and/or if the current drivers 623a and 623b are designed to deliver different amounts of current (e.g., one current driver employing transistors having a different gate periphery than the other current driver). The circuit 620 is operational during the electroplating process to control the height and other dimensions of the power and sensor studs formed from the plating pads 615 and 616.

In this embodiment, both plating techniques have been implemented with five variable low current sinks used to control the current at each plating pad on some of the die, with a maximum permissible average current of 650 $\mu A/mm^2$. The remaining two bus lines of 612 are used for on-chip CMOS current sinks on other die on the wafer. One of these lines provides low voltage power and the other line is used to enable and define the value of the on-chip current sinks. A variable enable voltage supply is used and the total current is monitored and set to ensure that the maximum average DC current is less that 650 $\mu A/mm^2$ in the preferred embodiment. The on-chip CMOS approach largely overcomes problems associated with metal-to-metal via resistance variations since the plating current is determined by the drain-to-source current ($I_{ds}$) of transistors 623a or 623b. $I_{ds}$ is in turn determined by the characteristics of the transistor and the value of the resistor 621a or 621b connecting it to the enable voltage. This resistor 621a or 621b can be chosen to dominate the resistance of any metal-to-metal vias or metal-to-resistor contacts. Further preferred, polysilicon resistors are implemented to provide minimum resistance variation across the wafer.

Figure 6C:
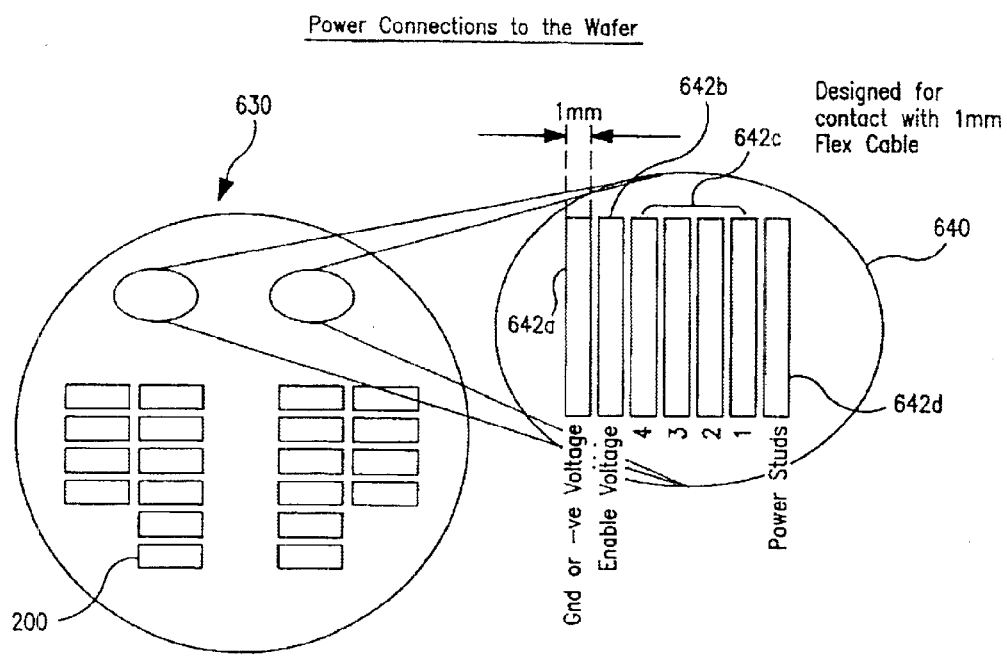
FIG. 6C illustrates a wafer power interface in accordance with one embodiment of the present invention.

FIG. 6C illustrates a wafer power interface in accordance with one embodiment of the present invention. As illustrated, the wafer 630 includes two power interfaces 640, each power interface 640 providing power to one half of the wafer. In alternative embodiments, a different number of interfaces 640 may be used.

Each power interface 640 includes conductive strips 642 for contact with probe needles, flex cable, or other connecting devices. In the illustrated embodiment, seven conductive strips 642 are provided corresponding to the seven electroplating bus lines 612 shown in FIG. 6A. Specifically, a first conductive strip 642a provides the ground (or $-V_E$) potential, a second conductive strip 642b provides the enable voltage, each of four conductive strips 642c provides power to sensor stud plating pads 615–618, and a seventh conductive strip 642d provides power to the power stud plating pads 619a–d. Each conductive strip is preferably 1 mm×10 mm. The illustrated power interface 640 is but only one example of one possible structure and those of skill in the art will appreciate that power interface structures of differing structure and/or dimensions may be used as well.

In the preferred embodiment, the final CMOS processing step involves removing resist by ashing the resist in an oxygen plasma. This process grows an Al oxide 150–200 Å thick on the sensor stud and power pads which is preferably removed prior to the electroplating process. While the sensor studs 222 in the preferred embodiment consist of electroplated Cu over Al, those of skill will appreciate that other base and plating metals may be used alternatively.

Figure 7A:
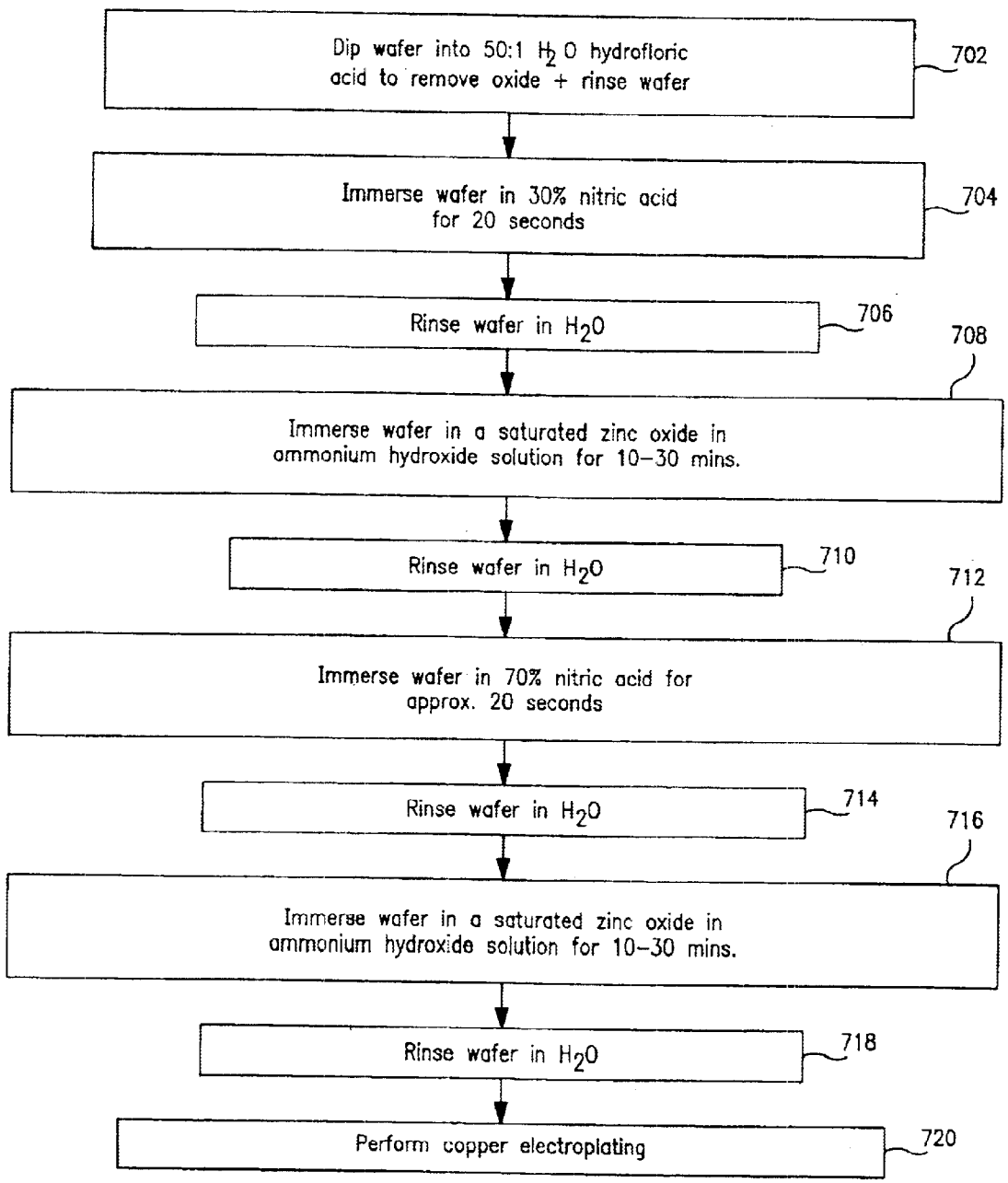
FIG. 7A is a flowchart illustrating the process by which electroplated copper sensor and power studs are formed in accordance with one embodiment of the present invention.

FIG. 7A is a flowchart illustrating the process by which electroplated Cu sensor and power studs 222 and 228 are formed in accordance with one embodiment of the present invention. The method is based on zincating based Cu electroplating techniques used with thick Al. This technique is very effective on bulk Al where a rather aggressive sodium hydroxide (NaOH) etch is used and a good zinc oxide layer is formed. Bulk Al electroplating techniques are not directly applicable to the thin Al films formed on CMOS IC's since the film is easily removed by the chemicals involved.

Initially at 702, the wafer is dipped into 50:1 water:hydrofluoric acid for approximately 120 seconds to remove the oxide formed during the resist ashing process and to lightly etch the Al surface. The wafer is then given a thorough rinse. Next at 704, the wafer is immersed in a 30% concentration of nitric acid for 20 seconds. Next at 706, the wafer is thoroughly rinsed in water.

At 708, the wafer is immersed in a saturated zinc oxide in ammonium hydroxide solution for 10–30 minutes, thereby forming a conductive zinc oxide layer. The immersion time will vary depending upon the thickness of the Al layer. The wafer is subsequently rinsed in water at 710.

Next at 712, the wafer is immersed in 70% nitric acid for approximately 20 seconds. This process operates to strip off the zinc oxide and does a final surface clean. The wafer is rinsed in water at 714 and subsequently immersed in the saturated zinc oxide in ammonium hydroxide solution for 10–30 minutes once more to grow the zinc oxide again at 716. A final quick rinse is performed at 718 and the wafer is quickly transferred to the Cu electroplating solution with the electrical connections already applied and powered up 720. The maximum average plating current is set to 650 $\mu$A/mm$^2$. Pulsed plating may be performed with a 10% duty cycle at 1 kHz. The Cu studs grow at roughly 1 $\mu$m/minute at this current density. Those of skill in the art we appreciate that other settings may be used as well.

Figure 7B:
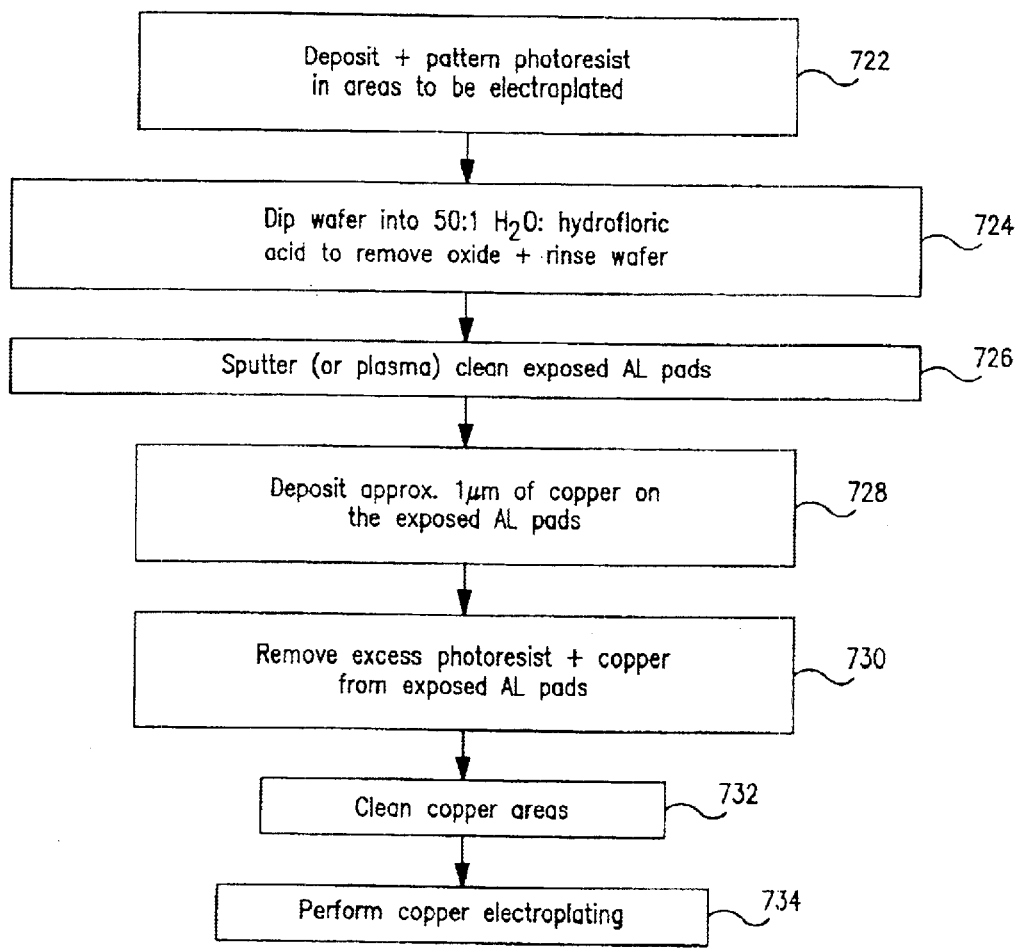
FIG. 7B is a flowchart illustrating a second method by which the electroplated copper sensor and power studs may be formed in accordance with the present invention.

FIG. 7B is a flowchart illustrating a second method by which the electroplated Cu sensor and power studs 222 and 228 may be formed in accordance with the present invention. This method deposits a seed layer of Cu onto oxide free Al sensor and power pads using a lift off process.

Initially at 722, photoresist is deposited and patterned to expose the Al areas where Cu is to be deposited. Next at 724, the wafer is dipped in 50:1 water:hydrofluoric acid for approximately 120 seconds and afterwards given a thorough rinse to remove the oxide formed during the resist ashing process. Next at 726, the exposed Al pads are sputter or plasma cleaned in the same equipment that the Cu is deposited in. Next at 728, without introducing air into the processing chamber approximately 1 $\mu$m of Cu is deposited on the exposed Al pads and photoresist. Next at 730, the resist and the excessive Cu covering the resist is removed, leaving the Cu on the exposed areas. Just prior to electroplating, the Cu surfaces are cleaned to remove any oxide.

In the preferred embodiment, Cu electroplating is performed by transferring the wafer to a Cu plating bath with electrodes and power already connected to the wafer prior to immersion in the bath. The maximum average plating current is set to 650 $\mu$A/mm$^2$ and pulsed plating performed with a 10% duty cycle at 1 kHz. The Cu studs grow at roughly 1 $\mu$m/minute at this current density. Those of skill in the art we appreciate that other settings may be used as well Each of the described methods may be implemented in various forms, including software, hardware, firmware, or a combination of these. In one embodiment of the present invention, the methods are implemented as software programs executable on a computer system, one embodiment of which is shown in FIGS. 4C and 4D. In this embodiment, the software program comprising the method is stored either locally in system memory 476, or on a fixed disk 486. In another embodiment, the program is stored on a removable disk 482, such as a magnetic floppy disk, a CD or DVD disk.

In a further embodiment, each method is implemented as a series of encoded electronic, electro-optic, or optical signals which are communicated to the computer system 460 via the network interface 488. The encoded electronic signals may be communicated to the network interface 488 via a hard-wire line such as a fiber optic or coaxial cable. Alternatively, the encoded signals may be communicated over free-space to the network interface 488. The network interface 488 in this embodiment is appropriately configured to receive and convert the encoded signals to computer-readable instructions corresponding to the processes illustrated in each of the present methods. The network interface may include electronic, electro-optic, or optically-based components such as an antenna or an electromagnetic lens, demodulation and/or demultiplexing circuitry and other similar components. The network interface may further include reciprocal circuitry and/or components operable to covert the processes of each of the present methods to encoded signals.

V. Applications

The present invention is applicable to a variety of adhesive bonding systems that incorporate an electrically insulating system between two metallic parts. The bonded metal can be two metal sheets or a metal sheet bonded over a metal honeycomb structure. In the later case, a small carrier insert would be required for location of the sensor within the honeycomb structure and an isolated electrical connection to the honeycomb would need to be designed into the bonding procedure.

The present invention also may be adapted for composite plates bonded to metal and/or composite plates or honeycomb with the inclusion of either a radio frequency power and communications interface to drive the sensor and CMOS circuits, or a two-wire interface that would produce minimal disruption to the composite structure. In the latter case, one or more sensor ICs could be serially connected along the wires. The two-wire interface can be implemented either as discrete, thin, insulated wires bond to the sensors or as a wiring pattern deposited and etched on a thin flexible substrate such as a polyimide sheet.

Aircraft

The driving factors behind aircraft structural maintenance are aircraft safety and longevity. Structural maintenance of military and commercial aircraft takes two forms: periodic replacement or inspect and repair. Some structural components of an aircraft are periodically replaced based on the number of takeoff/landing cycles experienced while other components are manually inspected and evaluated for repair or replacement. The inspect and repair method is very labor intensive and based upon arbitrary judgments, and both methods lead to cost inefficient maintenance.

Most commercial aircraft are manufactured using bonding technology to adhere certain external surfaces to their underlying structures. Typical components that use bonding technology include the rudder, elevators, ailerons, wing-to-fulselage fillet, nacelles, engine cowling, and rotors (helicopters). Newer aircraft use fiber reinforced materials for the honeycomb core with skins made of metallic or nonmetallic materials. Older aircraft generally use metallic materials in a monolithic construction.

The market opportunity related to aircraft is to provide NDI of adhesive bonded structures. The concept is to produce a "smart material" consisting of a number of small, independent, wireless sensor ICs embedded within the adhesive bond-line. The "smart material" can be retrofitted as part of a structural repair or when an aircraft goes through a complete tear down during the Life Extension Program. A longer-term opportunity is also to embed the "smart material" during new aircraft construction. During maintenance, the "smart materials" are connected to a central control unit which indicates the status of each embedded sensor IC and identifies weak or damaged locations.

This approach allows aircraft structural inspection to be achieved without removal of assemblies from the aircraft and saves maintenance time, reduces the cost of structural inspection, provides consistency, reduces the variety of required inspection equipment, and produces an earlier warning of bond degradation. A reliable test for partial bond degradation would also lead to wider application of bonding technology and improved understanding of degradation mechanisms.

Bridges

The driving factors behind highway bridge maintenance are safety and highway maintenance budget allocation. The Federal Highway Administration (FHWA) requires that each bridge in the United States be inspected every two years and rated on a scale of 0 to 9. The condition rating assigned to a bridge is based on a manual inspection of the bridge which is a time-consuming, labor intensive, and often arbitrary process. Nonetheless, the decision for maintenance on a bridge is based largely upon the rating it receives.

There are many bridge designs in existence today including prestressed concrete multi-beam, girder floorbeam, slab span, concrete tee beam, adjacent box beam, steel box girder, reinforced concrete frame, deck truss, through truss, deck arch, through arch, suspension, cable-stayed, bascule, steel culvert, and concrete box culvert. Many of these bridge types involve encapsulating a steel superstructure in concrete, thereby eliminating the ability to determine the condition of the steel superstructure.

The market opportunity for bridges is to provide automatic, Non-Destructive Monitoring of the corrosion condition of bridge elements. The concept is to place a number of sensors (similar to those for aircraft) within the surrounding concrete placed near the reinforcing steel rebar cage. Wireless sensor ICs can be placed as a "sensor cluster" during bridge column overhaul or by inserting a concrete core with an embedded sensor cluster into small diameter holes drilled through the bridge element. The sensor ICs allow bridge managers to quickly, consistently, and cost-effectively determine the corrosion state at each location of the bridge element. This approach allows bridge corrosion evaluation to be achieved without costly manual inspection, increases the thoroughness of the inspection, provides consistent results, reduces the variety of required inspection equipment, and produces an earlier warning of bridge deterioration.

The present invention has been described above in terms of a presently preferred embodiment so that an understanding of the present invention can be conveyed. There are, however, many configurations for bond integrity-sensing systems not specifically described herein but with which the present invention is applicable. The present invention should therefore not be seen as limited to the particular embodiments described herein, but rather, it should be understood that the present invention has wide applicability with respect to bond integrity sensing systems generally. All modifications, variations, or equivalent arrangements and implementations that are within the scope of the attached claims should therefore be considered within the scope of the invention.

What is claimed is:

1. An on-wafer electroplating control circuit for controlling the formation of an electroplated structure, the on-wafer electroplating control circuit comprising:
   an on-wafer resistor having a first port and a second port; and
   an on-wafer current driver having a first port coupled to the second port of the on-wafer resistor and a second port coupled to a plating pad, the on-wafer current driver configured to provide a predefined current to the plating pad responsive to the application of an enable voltage at the first port of the on-wafer resistor.

2. The on-wafer electroplating control circuit of claim 1, wherein the on-wafer resistor comprises a polysilicon resistor and wherein the current driver comprises a two FET current mirror.

3. An on-wafer electroplating control circuit for controlling the formation of an electroplated structure, the on-wafer electroplating control circuit comprising:
   an on-wafer resistor having a first port and a second port;
   an on-wafer current driver having a first port coupled to the second port of the on-wafer resistor and a second port coupled to a plating pad, the on-wafer current driver configured to provide a predefined current to the plating pad responsive to the application of an enable voltage at the first port of the on-wafer resistor
   a second on-wafer resistor having a first port coupled to the first port of the on-wafer resistor and a second port; and
   a second on-wafer current driver having a first port coupled to the second port of the second on-wafer resistor and a second port coupled to a second plating pad, the second on-wafer current driver configured to provide a predefined current to the second plating pad responsive to the application of the enable voltage at the first port of the on-wafer resistor.

\* \* \* \* \*

UNITED STATES PATENT AND TRADEMARK OFFICE
CERTIFICATE OF CORRECTION

PATENT NO.    : 6,693,417 B2
DATED         : February 17, 2004
INVENTOR(S)   : Alan Wilson It is certified that error appears in the above-identified patent and that said Letters Patent is hereby corrected as shown below:

<u>Column 10,</u>
Line 10, "computer system 460 470" should read as -- computer system 470. --.

Signed and Sealed this

Fifteenth Day of June, 2004

JON W. DUDAS
*Acting Director of the United States Patent and Trademark Office*